(12) United States Patent
Wagner

(10) Patent No.: US 11,545,678 B2
(45) Date of Patent: Jan. 3, 2023

(54) TEST CHAMBER AND CONTROL METHOD

(71) Applicant: Weiss Umwelttechnik GmbH, Reiskirchen (DE)

(72) Inventor: Enno Wagner, Mainz (DE)

(73) Assignee: WEISS TECHNIK GMBH, Reiskirchen (DE)

( * ) Notice: Subject to any disclaimer, the term of this patent is extended or adjusted under 35 U.S.C. 154(b) by 573 days.

(21) Appl. No.: 16/674,688

(22) Filed: Nov. 5, 2019

(65) Prior Publication Data
US 2020/0144637 A1 May 7, 2020

(30) Foreign Application Priority Data

Nov. 7, 2018 (EP) .................................. 18204943

(51) Int. Cl.
*F24F 11/80* (2018.01)
*F24F 11/00* (2018.01)
(Continued)

(52) U.S. Cl.
CPC ..... *H01M 8/04089* (2013.01); *F24F 11/0001* (2013.01); *F24F 11/0008* (2013.01);
(Continued)

(58) Field of Classification Search
CPC ............... F24F 2110/76; F24F 11/0008; F24F 11/0001; F24F 11/80
See application file for complete search history.

(56) References Cited

U.S. PATENT DOCUMENTS

| | | | | |
|---|---|---|---|---|
| H229 | H | * | 3/1987 | Phillips .................... F24F 11/30 374/134 |
| 4,967,608 | A | * | 11/1990 | Yost ..................... G01N 1/2205 73/866 |

(Continued)

FOREIGN PATENT DOCUMENTS

| | | |
|---|---|---|
| DE | 20013299 U1 | 12/2000 |
| JP | 2017219370 A * | 12/2017 |

OTHER PUBLICATIONS

Jorissen, et al., Fuel Cell Testing, In Fuel Cells for Stationary, Automotive and Portable Applications, 2001, pp. 1-19.

(Continued)

*Primary Examiner* — Nelson J Nieves
(74) *Attorney, Agent, or Firm* — Quarles & Brady LLP

(57) ABSTRACT

A method for controlling a climate test chamber for conditioning air and a test chamber includes a fuel cell assembly exposed to at least one physical test condition in a test space. The fuel cell assembly includes at least one electrochemical fuel cell having an anode compartment and a cathode compartment each having a feed opening for introducing reactants and a discharge opening for discharging waste products of the fuel cell assembly. The fuel cell assembly is operated in the test space, and a fuel gas and an oxidation gas is fed to the fuel cell assembly as reactants. The test space is supplied with conditioned supply air and exhaust air is discharged from the test space by an air conditioning and ventilation system. An oxygen concentration is determined using a sensor and a controller controls the oxygen concentration.

20 Claims, 1 Drawing Sheet

(51) Int. Cl.
*F24F 110/76* (2018.01)
*H01M 8/04089* (2016.01)
*H01M 8/04291* (2016.01)
*G01N 33/00* (2006.01)

(52) U.S. Cl.
CPC ......... *F24F 11/80* (2018.01); *H01M 8/04291* (2013.01); *F24F 2110/76* (2018.01); *G01N 33/0036* (2013.01)

(56) References Cited

U.S. PATENT DOCUMENTS

| | | | | | |
|---|---|---|---|---|---|
| 6,471,136 | B1* | 10/2002 | Chatterjee | ......... | G01N 21/7703 237/2 B |
| 2002/0035927 | A1* | 3/2002 | Kutt | ........................ | F24F 11/30 96/111 |
| 2002/0127965 | A1* | 9/2002 | Leeds | ...................... | F24F 11/74 454/306 |
| 2011/0150697 | A1* | 6/2011 | Okano | ................... | F24F 8/192 422/4 |
| 2013/0047706 | A1* | 2/2013 | Kim | ........................ | G01F 1/44 73/40 |
| 2016/0356521 | A1* | 12/2016 | Bertini | ................. | F24F 13/029 |
| 2018/0024105 | A1* | 1/2018 | Damazo | ................ | G01N 33/22 436/126 |
| 2018/0187906 | A1* | 7/2018 | Bahar | ................. | F24F 3/1417 |
| 2019/0041076 | A1* | 2/2019 | Prewer | ..................... | F24F 6/14 |
| 2019/0245227 | A1* | 8/2019 | Kim | ................. | H01M 8/04843 |
| 2022/0010992 | A1* | 1/2022 | Lai | ............................ | F24F 8/22 |

OTHER PUBLICATIONS

ESPEC Corp., Temperature Chamber Series, Product Brochure, Apr. 2018, 24 pages.

* cited by examiner

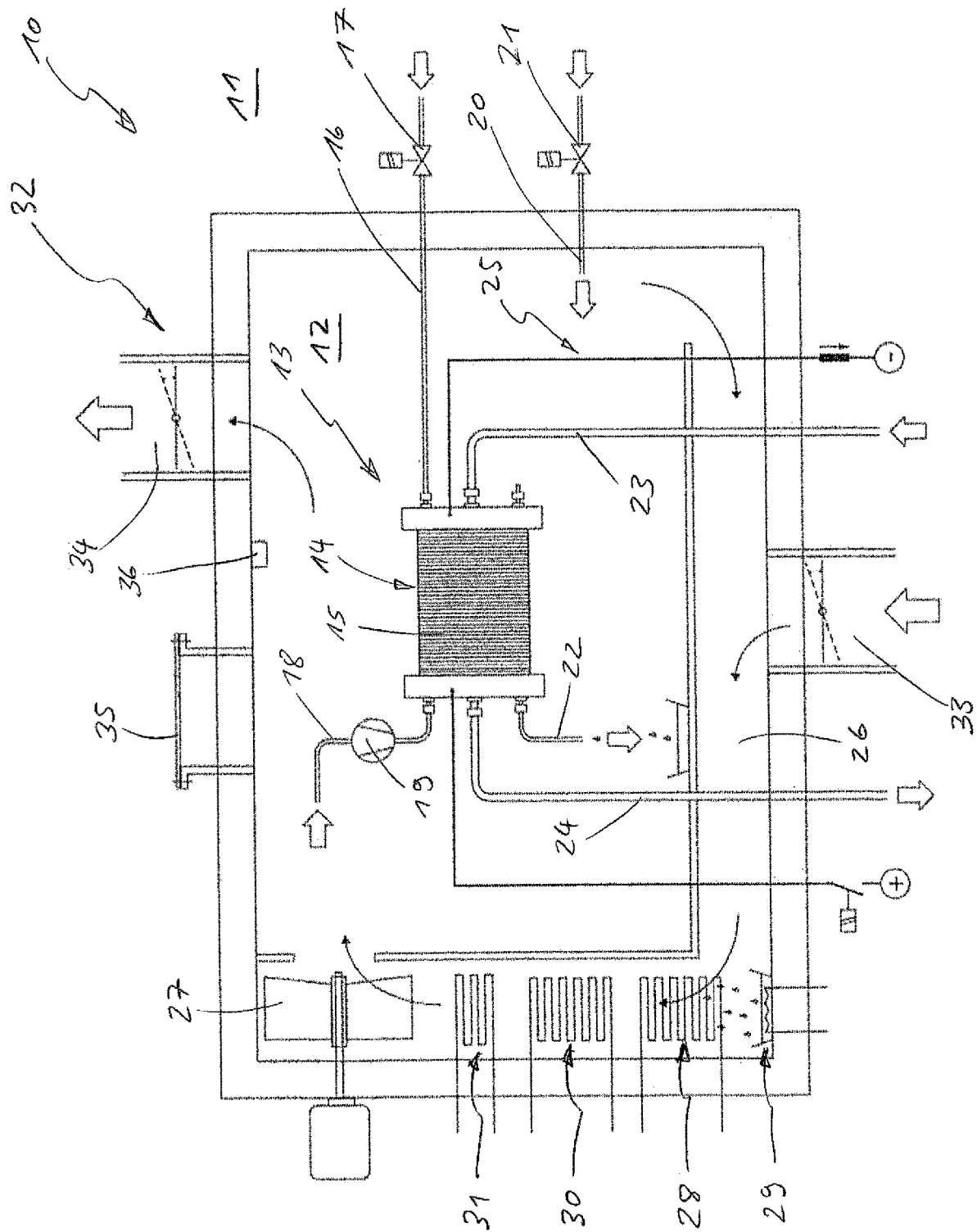

TEST CHAMBER AND CONTROL METHOD

This application claims priority to European Patent Application No. 18204943.7 filed Nov. 7, 2018. The contents of this application are hereby incorporated by reference as if set forth in their entirety herein.

The disclosure relates to a test chamber, in particular a climate chamber for conditioning air, and to a method for controlling a test chamber, a fuel cell assembly being exposed to at least one physical test condition in a test space of the test chamber, the fuel cell assembly comprising at least one electrochemical fuel cell having an anode compartment and a cathode compartment each having a feed opening for introducing reactants and a discharge opening for discharging waste products of the fuel cell assembly, the fuel cell assembly being operated in the test space, a fuel gas and an oxidation gas present in the test space being fed to the fuel cell assembly as reactants, the test condition being set by open-loop and/or closed-loop control of an air temperature, an air pressure and a relative humidity in the test space by means of a control device of the test chamber, the test space being supplied with conditioned supply air and exhaust air being discharged from the test space by means of an air conditioning and ventilation system of the test chamber.

Test chambers of this kind are typically used to test physical and/or chemical properties of objects, in particular devices. For instance, temperature test cabinets or climate test cabinets are known in which temperatures in a range of −70° C. to +180° C. can be set. In climate test cabinets, desired climatic conditions can additionally be set, to which the device or the test material is then exposed for a predefined period of time. The temperature of the test space receiving the test material to be tested is typically controlled in a circulating air duct within the test space. The circulating air duct forms an air treatment space in the test space, in which heat exchangers for heating or cooling the air flowing through the circulating air duct or the test space are disposed. A fan or ventilator aspirates the air present in the test space and conducts it to the respective heat exchangers in the circulating air duct. In this way, the test material can be temperature-controlled or can be exposed to a defined change in temperature. Thus, a temperature can change between a maximum temperature and a minimum temperature of the test chamber during a test cycle.

Furthermore, it is known for what is referred to as fuel cells or fuel cell assemblies to be exposed to defined climatic conditions in such a test chamber in order to test a performance or a function of the fuel cell assembly, for example. The fuel cell assemblies or fuel cells known from the state of the art are known to have an electrolyte membrane with an anode and a cathode and, for example, hydrogen as a fuel gas and oxygen as an oxidation gas.

As solid polymer fuel cells, they are typically composed of a polymeric ion exchange membrane having a coating on both sides which forms an electrolyte catalyst and which is made of an electrically conductive layer material, which forms the anode and the cathode. Two electrically conductive separator plates cover the electrolyte membrane on both sides, the separator plates forming channels via which the reactants are suitably distributed across the respective surfaces of the electrolyte membrane.

Furthermore, the separator plates serve as current collectors in the area of the anode and the cathode. Since an output voltage that can be achieved using a conventional fuel cell is relatively low, fuel cells are connected in series, i.e. arranged in stacks, to achieve higher output voltages. In that case, the separator plates are realized as a bipolar plate having channels formed on both sides for channeling and distributing the reactants. The channels on the anode side and on the cathode side are each supplied with fuel gas and oxidation gas, respectively, via a single feed opening, waste products being discharged via respective singular discharge openings.

If a fuel cell assembly having electrolyte membranes is operated with hydrogen as the fuel gas, process water and condensate will typically accumulate in the anode compartment during operation of the fuel cell assembly, the anode compartment being regularly purged to prevent flooding of the anode compartment. The water present in the anode compartment and the fuel gas contained therein will enter an environment of the fuel cell assembly, i.e. the test space. If the fuel gas is hydrogen, this may lead to the formation of oxyhydrogen gas in the test space, which is why the air in the test space has to be exchanged by means of the air conditioning and ventilation system. Also, fuel cell assemblies are known in which hydrogen as the fuel gas is circulated and foreign products loading the hydrogen have to be separated. Conditioned supply air is supplied and exhaust air is discharged in the test space by means of the air conditioning and ventilation system. To this end, ducts for the supply air and the exhaust air are connected to the test space.

To test the fuel cell assembly, it is connected to an electronic load, allowing current-voltage characteristics to be detected based on an increase or decrease in electrical resistance. The test space and the air conditioning and ventilation system connected therein are hermetically sealed from an ambient air of the test space, the cathode of the fuel cell assembly being supplied with oxygen as the oxidation gas from the test space.

Ideal setting of the relative humidity in the test space is substantial for an ideal functioning of the fuel cell assembly within the test space. When the air present in the test space is fed to the fuel cell assembly with oxygen as the oxidation gas, it must not be too humid or too dry because otherwise the power density of the fuel cell assembly decreases severely. Also, the supply air provided by the air conditioning and ventilation system has to be suitably preconditioned in terms of air temperature. The components of the air nut usable as oxidation gas, such as nitrogen, have to be suitably conditioned, as well. Hence, the air conditioning and ventilation system has to be equipped with high-power driers and humidifiers if the air required for the necessary air exchange is to be suitably conditioned. Furthermore, the test space may be pressurized by means of the air conditioning and ventilation system, thereby increasing the air flow rate even further.

Hence, the object of the present disclosure is to propose a method and a test chamber comprising a fuel cell assembly that allow simple and cost-effective testing of a fuel cell assembly. This object is attained by a method having the features of claim 1 and by a device having the features of claim 19.

In the method according to the disclosure for controlling a test chamber, in particular a climate chamber for conditioning air, a fuel cell assembly is exposed to at least one physical test condition in a test space of the test chamber, the fuel cell assembly comprising at least one electrochemical fuel cell having an anode compartment and a cathode compartment each having a feed opening for introducing reactants and a discharge opening for discharging waste products of the fuel cell assembly, the fuel cell assembly being operated in the test space, a fuel gas and an oxidation gas present in the test space being fed to the fuel cell assembly as reactants, the test condition being set by open-loop and/or closed-loop control of an air temperature, an air pressure and a relative humidity in the test space by means of a control device of the test chamber, the test space being supplied with conditioned supply air and exhaust air being discharged from the test space by means of an air conditioning and ventilation system of the test chamber, wherein an oxygen concentration is determined using a sensor of a controller of the control device in the test space, the controller controlling the oxygen concentration.

In the method according to the disclosure, the fuel cell assembly is disposed and operated in the test space of the test chamber. During operation, the fuel cell assembly is exposed to defined environmental conditions for a test period. An air exchange in the test space is realized in the air conditioning and ventilation system in order to remove any released fuel gas of the fuel cell assembly from the test space. In particular, the oxygen concentration in an air of the test space is determined, i.e. measured, by means of the sensor of the controller and is controlled according to the oxygen concentration required in the test space for operation of the fuel cell assembly. This allows an output of the air conditioning and ventilation system to be reduced until an oxygen concentration only just sufficient for operation of the fuel cell assembly is reached in the air of the test space. In this case, it is no longer necessary for the air conditioning and ventilation system to supply the test space with great amounts of preconditioned supply air because it has to introduce only as much (fresh) air in the test space as is actually needed by the fuel cell assembly. While the fuel cell assembly uses in particular the oxygen portion of the air as oxidation gas, the air conditioning and ventilation system has to suitably precondition the other air portions, such as nitrogen, as well. Since the method according to the disclosure allows the oxygen portion that is to be pumped by the air conditioning and ventilation system to be reduced, an amount of air significantly smaller by comparison will have to be pumped and treated by the air conditioning and ventilation system as a result. In addition to the amount of energy that can be saved in this way, the air conditioning and ventilation system and in particular the humidifiers, dehumidifiers and heat exchangers needed to treat the supply air can be smaller in dimension by comparison, allowing a significant amount of costs to be saved.

The air conditioning and ventilation system can be controlled by the control device. The control device can receive data or signals regarding the oxygen concentration in the test space from the controller. Thus, the controller can form a closed-loop controlled system with the control device. In that case, the control device can control the air conditioning and ventilation system to precondition the supply air and control the test space to condition the air in the test space, in particular the air temperature and the relative humidity, for example. This closed-loop control can be effected by means of a PID controller. The controller of the control device can increase or reduce an air exchange in the test space by controlling the air conditioning and ventilation system in order to control the oxygen concentration.

It is particularly advantageous if oxygen is introduced into the test space and/or into a supply duct of the air conditioning and ventilation system as a function of the oxygen concentration using a metering valve of the controller. For example, pure oxygen can then be introduced directly into the test space via a supply line. The oxygen consumed by the fuel cell assembly can be replenished with the oxygen introduced in the test space. Thus, the oxygen no longer needs to be introduced into the test space by way of the supply air, which means that a substantially lower amount of supply air has to be preconditioned by the air conditioning and ventilation system. Hence, the air conditioning and ventilation system can be of an even smaller size. Alternatively or additionally, pure oxygen may be introduced into the supply air duct of the air conditioning and ventilation system so that the supply air has a greater oxygen content. Thus, said oxygen is preconditioned already. Consequently, the remaining portion of the air components, which cannot be used as oxidation gas by the fuel cell assembly, is smaller. Overall, the test space has to be supplied with comparably less conditioned supply air by the air conditioning and ventilation system. The metering valve allows relatively precise metering of the actually needed amount of oxygen into the test space or the supply air duct, the amount of air to be conditioned thus being reduced to a minimum. The metering valve can be an electronic regulating valve, for example.

Furthermore, the waste products may be discharged into the test space. The waste products may contain water, steam and fuel gas residue, for example. The waste products can then be discharged from the test space by means of the exhaust air of the air conditioning and ventilation system. Furthermore, the waste products, in particular the steam, can be used to set the humidity in the test space. At least, this ensures that the fuel cell assembly is tested under realistic environmental conditions.

The cathode compartment can be supplied with air present in the test space by means of a pump of the fuel cell assembly. Said air will have the oxygen concentration measured by means of the sensor or the oxygen concentration controlled by the controller in the test space. For example, the pump may be a compressor, which is required anyway to operate the fuel cell assembly.

The anode compartment can be supplied with hydrogen as a fuel gas by means of a fuel gas metering valve of the fuel cell assembly. In this way, pure hydrogen ($H_2$) can be fed directly to the fuel cell assembly via a supply line. The fuel gas metering valve can be an electronic regulating valve. The chemical equation of the fuel cell $$H_2 + \tfrac{1}{2}O_2 \rightarrow H_2O + E_{el}$$

results in a hydrogen/oxygen ratio of 2:1, allowing the required amount of oxygen to be introduced into the test space very precisely as a function of the amount of hydrogen by means of the controller. The amount of air to be conditioned can be reduced even further in this way.

The hydrogen ($H_2$) and the oxygen ($O_2$) can also be produced by means of an electrolyzer located in the test space. For example, a pressure electrolyzer may be disposed in the test space, said pressure electrolyzer producing and discharging into the test space the amount of hydrogen and oxygen consumed by the fuel cell assembly. Thus, a complex installation of hydrogen and oxygen supply lines and the accompanying storage can be entirely omitted. All that is required is for the pressure electrolyzer to be supplied with electrical energy within the test space. In principle, it is also possible for the pressure electrolyzer to be disposed outside the test space and for hydrogen and oxygen to be introduced into the fuel cell assembly via supply lines or into the test space via a supply air duct of the air conditioning and ventilation system.

The air temperature in the test space can be set by means of a temperature control device of the test chamber. This allows the temperature of the preconditioned supply air to be controlled even more precisely. In this case, the air temperature in the test space is controlled by means of the control device. An air treatment space, in which the heat exchangers for heating or cooling the air flowing through the test space are disposed, may be formed in the test space. Furthermore, a fan or ventilator for circulating the air present in the test space may be provided, the air treatment space thus being realized in the manner of a circulating air duct.

The relative humidity in the test space can be set using a humidifier and/or a dehumidifier of the test chamber which are/is disposed in the test space. The humidifier or dehumidifier can be disposed in an air treatment space in the test space. In this case, the control device can control a relative humidity in the test space relatively precisely via the humidifier or dehumidifier. Likewise, the air conditioning and ventilation system can have humidifiers and/or dehumidifiers for preconditioning the supply air.

The relative humidity in the test space can be measured using a humidity sensor of a humidifier control circuit of the control device. This allows particularly precise control and setting of a relative humidity in the test space.

The air pressure in the test space can be set by means of a supply air blower and/or an exhaust air blower of the air conditioning and ventilation system. For example, this also allows pressure higher than an ambient pressure to be established in the test space. Since an air pressure would be variable in a closed test space by introducing fuel gas and by the consumption of oxidation gas, this also ensures that a constant air pressure can be set in the test space at all times. The supply air blower and the exhaust air blower can be controlled by means of the control device.

In this way, an air exchange rate in the test space and/or a pressure difference between the test space and an environment can be established by means of the air conditioning and ventilation system. The air exchange rate can be set in such a manner that a non-ignitable amount of fuel gas is present in the test space at all times.

The air temperature and/or the relative humidity of the supply air can also be set by means of the air conditioning and ventilation system. In this case, the air conditioning and ventilation system will comprise a humidifier and/or a dehumidifier and a heat exchanger for controlling the temperature of the supply air. The air conditioning and ventilation system can precondition the supply air according to the test condition desired for the fuel cell assembly. The test condition can be precisely set within the test space itself by conditioning the air present in the test space.

It is particularly advantageous if an electric current generated by the fuel cell assembly can be measured, the control device being capable of controlling the relative humidity as a function of the generated current. The measured electric current and an amount of water produced by the fuel cell assembly depend on each other according to Faraday's law:

$$n_{H2O,prod} = I/(n+F)$$

I=electric current
n=2
F=96485 C/mol (Faraday constant)

A substance flow of the water or steam produced by the fuel cell assembly can thus be determined directly and in real time by means of the control device. Also, the produced amount of water thus measured can be used to pilot-control a humidity controller of the control device to set the relative humidity in the test space and/or in the conditioned supply air. Overall, this allows the relative humidity in the test space and/or of the supply air to be controlled even more precisely as a function of the generated current.

Alternatively or additionally, an electrical current generated by the fuel cell assembly can be measured, the controller being capable of controlling the oxygen concentration as a function of the generated current. According to Faraday's law stated above and according to the chemical equation of the fuel cell assembly, the amount of oxygen consumed from the test space to generate the measured electric current can be determined very precisely in that case. The test space can then be supplied with the required amount of said oxygen with corresponding precision. The thus determined amount of oxygen consumed can be employed to pilot-control the controller in order to control the oxygen concentration, for example.

Furthermore, the measured electric current can be used as an input parameter of a master controller of a cascade control of the control device. The cascade control can comprise, among other components, a PID controller for controlling the air temperature, the air pressure and/or the humidity in the test space. The control device can take a relative humidity increased by the output of steam of the fuel cell assembly and a consumption of oxygen into account as control parameters, making testing of a fuel cell assembly by means of a test chamber significantly simpler. Time-consuming parameterization and presetting of these variables at the control device of the test chamber is no longer necessary in that case.

It is also particularly advantageous if the controller is used as a slave controller of the cascade control. In this way, control precision can be improved even further.

The physical test condition can be a temperature, a relative humidity, a corrosive atmosphere and/or a component strength. Furthermore, the fuel cell assembly may be operated for a test period and may be exposed to said test condition under load.

The test chamber, in particular climate chamber, according to the disclosure for conditioning air comprises a test space which can be sealed against an environment and which is temperature-insulated, the test space having disposed therein a fuel cell assembly which is operable in the test space and exposable to at least one climatic test condition, the fuel cell assembly comprising at least one electrochemical fuel cell having an anode compartment and a cathode compartment each having a feed opening for introducing reactants and a discharge opening for discharging waste products of the fuel cell assembly, a fuel gas and an oxidation gas present in the test space being fed to the fuel cell assembly as reactants, the test chamber having a control device for setting the test condition by open-loop and/or closed-loop control of an air temperature, an air pressure and a relative humidity in the test space, the test chamber having an air conditioning and ventilation system for introducing conditioned supply air into the test space and for discharging exhaust air from the test space, wherein the control device has a controller having a sensor for determining an oxygen concentration in the test space, the controller being configured to control the oxygen concentration in the test space. Regarding the advantageous effects of the test chamber according to the disclosure, reference is made to the description of advantages of the method according to the disclosure.

The test chamber can have a temperature control device for controlling the temperature of the test space, wherein a temperature in a temperature range of −70° C. to +180° C., preferably −80° C. to +200° C., may be establishable within the test space by means of the temperature control device, the temperature control device may comprise a cooling unit having a cooling circuit comprising a refrigerant, a heat exchanger disposed in the test space, a compressor, a condenser and an expansion element, and the temperature control device can have a heating unit comprising a heater and another heat exchanger.

In this case, it becomes possible to cool a circulated amount of air of the test space by means of the cooling unit via the heat exchanger in the test space. The heat exchanger can be connected to or be integrated in the cooling circuit, the refrigerant circulating in the cooling circuit thus flowing through the heat exchanger. The compressor can be a mechanical compressor device, and the condenser for the condensed refrigerant can be connected downstream of the compressor in the flow direction of the refrigerant. The refrigerant liquefied in the condenser can flow via the expansion element so that it turns gaseous again by expansion due to a pressure drop and cools the heat exchanger. The heating unit or the heater can be composed of electrical heating elements via which the other heat exchanger can be heated. Like the heat exchanger, the other heat exchanger can be disposed within the test space.

Other advantageous embodiments of the test chamber are apparent from the description of features of the claims dependent on method claim 1.

Hereinafter, the disclosure will be explained in more detail with reference to the accompanying drawing.

The FIGURE shows a schematic illustration of a test chamber 10 having a temperature-insulated test space 12 which is hermetically sealed against an environment 11. A fuel assembly 13 composed of a stack 14 of fuel cells 15 is disposed in test space 12. Fuel cell assembly 13 can be supplied directly with hydrogen ($H_2$) as a fuel gas via a supply line 16 having a fuel gas metering valve 17. Furthermore, fuel cell assembly 13 can be supplied with air present in test space 12 via a supply line 18 having a compressor 19. Moreover, oxygen ($O_2$) as an oxidation gas can be supplied via a supply line 20 having a metering valve 21. Waste products of fuel cell assembly 13, such as fuel gas residue, water and/or steam, are discharged into test space 12 via a discharge line 22.

Fuel cell assembly 13 is cooled by means of cooling water, the cooling water being fed to fuel cell assembly 13 via a feed line 23 and, after having flown through stack 14, being discharged via a return line 24. Fuel cell assembly 13 is connected to a circuit 25 via which a load can be generated and current and voltage can be measured.

A circulating air duct 26 through which air present in test space 12 can be circulated by means of a fan 27 is formed within test space 12. A dehumidifier 28, a humidifier 29, a heat exchanger 30 for cooling air and another heat exchanger 31 for heating air are disposed in circulating air duct 26. A supply air duct 33 and an exhaust air duct 34 of an air conditioning and ventilation system 32, which is shown only in part, are connected to test space 12. Via supply air duct 33, preconditioned supply air can be introduced directly into circulating air duct 26 and thus into test space 12. The air present in test space 12 is discharged via exhaust air duct 34. Furthermore, a rupture disk 35 is connected to test space 12. Moreover, a sensor 36 for measuring an oxygen concentration in test space 12 is disposed in test space 12. Sensor 36 is part of a controller (not shown) for controlling the oxygen concentration. The controller controls metering valve 21 in such a manner that, by supplying oxygen via feed line 20, the oxygen concentration within test space 12 is always set in a way that allows fuel cell assembly 13 to be operated. Thus, the oxygen of the air in test space 12 that is consumed by fuel cell assembly 13 can be replenished via feed line 20 without having to introduce large amounts of preconditioned air via supply air duct 33.

The controller is part of a control device (not shown) of test chamber 10, the control device controlling air conditioning and ventilation system 32, fan 27, dehumidifier 28, humidifier 29, heat exchanger 30 and heat exchanger 31 to condition the air present in test space 12. By measuring the current generated by fuel cell assembly 13, the control device can calculate an amount of waste products or water produced and/or oxygen consumed by fuel cell assembly 13. The control device can then control air conditioning and ventilation system 32, dehumidifier 28, humidifier 29 and metering valve 21 with according precision. Overall, this leaves the amount of air having to be circulated by air conditioning and ventilation system 32 small, and a humidification and dehumidification of air can essentially be limited to the oxygen portion of the air present in test space 12. Moreover, complex parameterization of the control device prior to the performance of a test using fuel cell assembly 13 can be omitted because the relevant variables can be determined by the control device itself.

The invention claimed is:

1. A method for controlling a climate test chamber for conditioning air, a fuel cell assembly being exposed to at least one physical test condition in a test space of the test chamber, the fuel cell assembly comprising at least one electrochemical fuel cell having an anode compartment and a cathode compartment each having a feed opening for introducing reactants and a discharge opening for discharging waste products of the fuel cell assembly, the fuel cell assembly being operated in the test space, a fuel gas and an oxidation gas present in the test space being fed to the fuel cell assembly as reactants, the test condition being set by open-loop and/or closed-loop control of an air temperature, an air pressure and a relative humidity in the test space by a control device of the test chamber, the test space being supplied with conditioned supply air and exhaust air being discharged from the test space by an air conditioning and ventilation system of the test chamber, comprising the steps of: determining an oxygen concentration using a sensor of a controller of the control device in the test space, and controlling the oxygen concentration with the controller.

2. The method according to claim 1, further comprising the step of controlling the air conditioning and ventilation system with the control device.

3. The method according to claim 1 further comprising the step of introducing oxygen ($O_2$) into the test space and/or into a supply air duct of the air conditioning and ventilation system as a function of the oxygen concentration using a metering valve of the controller.

4. The method according claim 1, further comprising the step of discharging the waste products into the test space.

5. The method according to claim 1, further comprising the step of supplying the cathode compartment with air present in the test space with a pump of the fuel cell assembly.

6. The method according to claim 1, further comprising the step of supplying the anode compartment with hydrogen ($H_2$) as a fuel gas with a fuel gas metering valve of the fuel cell assembly.

7. The method according to claim 6, further comprising the step of producing the hydrogen ($H_2$) and the oxygen ($O_2$) are produced with an electrolyzer located in the test space.

8. The method according to claim 1, further comprising the step of setting the air temperature in the test space with a temperature control device of the test chamber.

9. The method according to claim 1, further comprising the step of setting the relative humidity in the test space is set with a humidifier and/or a dehumidifier of the test chamber, the humidifier and/or the dehumidifier being located in the test space.

10. The method according to claim 1, further comprising the step of measuring the relative humidity in the test space with a humidity sensor of a humidifier control circuit of the control device.

11. The method according to claim 1, further comprising the step of setting the air pressure in the test space is with a supply air blower and/or an exhaust air blower of the air conditioning and ventilation system.

12. The method according to claim 1, further comprising the step of using the air conditioning and ventilation system to establish an air exchange rate in the test space and/or a pressure difference between the test space and an environment.

13. The method according to claim 1, further comprising the step of setting the air temperature and/or the relative humidity of the supply air with the air conditioning and ventilation system.

14. The method according to claim 1, further comprising the steps of measuring an electric current produced by the fuel cell assembly and controlling the relative humidity with the control device as a function of the generated current.

15. The method according to claim 1, further comprising the steps of measuring an electric current produced by the fuel cell assembly and controlling the oxygen concentration with the controller as a function of the generated current.

16. The method according to claim 14, further comprising the step of using the measured electric current as an input parameter of a master controller of a cascade control of the control device.

17. The method according to claim 16, further comprising the step of using the controller as a slave controller of the cascade control.

18. The method according to claim 1, wherein the physical test condition is a temperature, a relative humidity, a corrosive atmosphere and/or a component strength.

19. A climate chamber for conditioning air, comprising a test space which can be sealed against an environment and which is temperature-insulated, the test space having disposed therein a fuel cell assembly which is operable in the test space and exposable to at least one physical test condition, the fuel cell assembly comprising at least one electrochemical fuel cell having an anode compartment and a cathode compartment each having a feed opening for introducing reactants and a discharge opening for discharging waste products of the fuel cell assembly, a fuel gas and an oxidation gas present in the test space being fed to the fuel cell assembly as reactants, the test chamber having a control device for setting the test condition by open-loop and/or closed-loop control of an air temperature, an air pressure and a relative humidity in the test space, the test chamber having an air conditioning and ventilation system for introducing conditioned supply air into the test space and for discharging exhaust air from the test space,
wherein
the control device has a controller having a sensor for determining an oxygen concentration in the test space, the controller being configured to control the oxygen concentration in the test space.

20. The test chamber according to claim 19, wherein the test chamber has a temperature control device for controlling the temperature of the test space, a temperature in a temperature range of −70° C. to +180° C. being establishable within the test space by means of the temperature control device, the temperature control device having a cooling unit comprising a cooling circuit comprising a refrigerant, a heat exchanger, which is disposed in the test space, a compressor, a condenser and an expansion element, the temperature control device having a heating unit comprising a heater and another heat exchanger.

* * * * *